(12) United States Patent
Yamakoshi et al.

(10) Patent No.: US 9,145,624 B2
(45) Date of Patent: *Sep. 29, 2015

(54) POLYMER COMPOSITION AND MOLDED ARTICLES SHAPED OF THE SAME

(75) Inventors: Shizuto Yamakoshi, Chiba (JP); Tatsuhiro Nagamatsu, Chiba (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/518,663

(22) PCT Filed: Dec. 25, 2009

(86) PCT No.: PCT/JP2009/071900
§ 371 (c)(1),
(2), (4) Date: Jun. 22, 2012

(87) PCT Pub. No.: WO2011/077592
PCT Pub. Date: Jun. 30, 2011

(65) Prior Publication Data
US 2012/0258158 A1 Oct. 11, 2012

(51) Int. Cl.
| | |
|---|---|
| *D01F 1/10* | (2006.01) |
| *A01N 25/10* | (2006.01) |
| *A01N 25/34* | (2006.01) |
| *C08K 5/00* | (2006.01) |
| *C08K 5/09* | (2006.01) |
| *C08L 23/06* | (2006.01) |
| *D01F 6/04* | (2006.01) |
| *A01N 53/00* | (2006.01) |
| *A01N 25/30* | (2006.01) |

(52) U.S. Cl.
CPC *D01F 1/10* (2013.01); *A01N 25/10* (2013.01); *A01N 25/34* (2013.01); *C08K 5/005* (2013.01); *C08K 5/09* (2013.01); *C08L 23/06* (2013.01); *D01F 6/04* (2013.01)

(58) Field of Classification Search
CPC ..... A61K 9/70; A61K 9/0014; A61K 9/0048; A61K 9/122
See application file for complete search history.

(56) References Cited

U.S. PATENT DOCUMENTS

| | | | |
|---|---|---|---|
| 3,806,561 A * | 4/1974 | Zviak et al. | 514/136 |
| 5,449,711 A | 9/1995 | Saito et al. | |
| 5,948,832 A | 9/1999 | Nagamatsu et al. | |
| 2002/0197292 A1 * | 12/2002 | Fowler | 424/401 |
| 2004/0077248 A1 * | 4/2004 | Kurahashi et al. | 442/401 |
| 2007/0264297 A1 * | 11/2007 | Scialdone et al. | 424/405 |
| 2009/0041680 A1 * | 2/2009 | Tamarkin et al. | 424/45 |

FOREIGN PATENT DOCUMENTS

| | | | |
|---|---|---|---|
| CN | 1236831 A * | 12/1999 | |
| GB | 2 170 211 A | 7/1986 | |
| JP | 61-176502 A | 8/1986 | |
| JP | 02045405 A * | 2/1990 | |
| JP | 4-145163 A | 5/1992 | |
| JP | 5-287133 A | 11/1993 | |
| JP | 06-315332 A | 11/1994 | |
| JP | 08-302080 A | 11/1996 | |
| JP | 9-77908 A | 3/1997 | |
| JP | 10-45944 A | 2/1998 | |
| JP | 2001-279033 A | 10/2001 | |
| JP | 2005053822 A * | 3/2005 | |
| JP | 2005-089676 A | 4/2005 | |
| JP | 2008-031431 A | 2/2008 | |
| JP | 2008-031619 A | 2/2008 | |
| JP | 2008-248090 A | 10/2008 | |
| JP | 2008-303348 A | 12/2008 | |
| JP | 2009-161739 A | 7/2009 | |
| WO | 2008/001926 A2 | 1/2008 | |
| WO | 2008/001927 A2 | 1/2008 | |
| WO | WO 2008032842 A2 * | 3/2008 | |
| WO | 2008/123593 A1 | 10/2008 | |
| WO | 2008121629 A1 | 10/2008 | |
| WO | 2008/153166 A1 | 12/2008 | |
| WO | 2009/075373 A1 | 6/2009 | |

OTHER PUBLICATIONS

Japanese Office Action dated May 7, 2013, issued in Japanese Patent Application No. 2009-287724.
Office Action issued Aug. 6, 2013 in counterpart Japanese Patent Application No. 2009-287724 with partial English translation.
Written Opinion and Search Report from the International Searching Authority issued on Mar. 30, 2010 in counterpart PCT Application No. PCT/JP2009/071900.

* cited by examiner

*Primary Examiner* — Sean Basquill
*Assistant Examiner* — Mark V Stevens
(74) *Attorney, Agent, or Firm* — Sughrue Mion, PLLC

(57) ABSTRACT

The present invention relates to a polymer composition comprising 100 parts by weight of an olefin-based polymer, and 0.01 to 100 parts by weight of a branched fatty acid and 0.01 to 200 parts by weight of a releasable active compound per 100 parts by weight of said olefin-based polymer.

11 Claims, No Drawings

POLYMER COMPOSITION AND MOLDED ARTICLES SHAPED OF THE SAME

CROSS REFERENCE TO RELATED APPLICATION

This application is National Stage of International Application No. PCT/JP2009/017900 filed Dec. 25, 2009, the contents of all of which are incorporated herein by reference in their entirety.

TECHNICAL FIELD

The present invention relates to a polymer composition and molded articles shaped of the polymer composition.

BACKGROUND ART

Polymer compositions which contain active compounds such as insecticides in polymers, and molded articles shaped of the same polymer compositions hitherto have been known and have been used in a wide rage of fields, since molded articles in various shapes can be obtained at relatively low costs. These molded articles exhibit their actions by allowing the active compounds to transpire, or by oozing the active compounds to the surfaces of the molded articles to thereby release the active compounds, i.e., so-called bleeding (cf. Patent Publication 1).

When an active compound having a low transpiring property is used, such a compound hardly releases from a molded article by its transpiration, and thus releases therefrom mainly by bleeding. Bleeding arises when the active compound in an amount exceeding a saturated amount to the polymer (an oversaturated amount) is retained in the molded article, and this is a phenomenon that the oversaturated amount of the active compound (=the amount of the active compound added−the saturated amount of the active compound in the molded article) migrates to the surface of the molded article with time. When a molded article is shaped of a polymer composition which contains an active compound in an amount exceeding a saturated amount, the active compound bleeds out to the surface of the molded article with time. However, it is generally known that this bleeding rate varies significantly depending on the amount of the active compound initially added, and this bleeding rate tends to decrease with time. On the other hand, when an molded article exhibits its action by way of bleeding of an active compound, a period of time during which a desired bleeding rate is obtained becomes an index for an effective period of the molded article. Therefore, once an effective period of the molded article has been determined, the amount of the releasable active compound initially added is inevitably determined.

To obtain a molded article usable over a long period of time, it is needed to use a polymer composition which contains an active compound in an amount exceeding saturated amount to a polymer. However, a molded article shaped of a polymer composition which contains an oversaturated amount of an active compound in a polymer permits a large amount of the active compound to bleed out at an early stage of use thereof, and thus, it is impossible to maintain a bleeding rate during a desired period of time.

Patent Publication 1: JP-A-6-315332

DISCLOSURE OF INVENTION

As a result of the present inventors' intensive studies, it is found that the use of an olefin-based polymer composition containing an olefin-based polymer, an active compound and a branched fatty acid is effective to prevent a decrease in the bleeding rate of the active compound, and that consequently, it becomes possible to increase the bleeding amount of the active compound during a given period of time. The present invention is accomplished based on this finding.

That is, the present invention provides a polymer composition comprising 100 parts by weight of an olefin-based polymer, and 0.01 to 100 parts by weight of a branched fatty acid and 0.01 to 200 parts by weight of a releasable active compound per 100 parts by weight of the olefin-based polymer.

The present invention further provides molded articles shaped of the above-described polymer composition.

According to the present invention, it is possible to prevent a decrease in the bleeding rate of the active compound, and therefore, it is possible to provide a polymer composition which makes it possible to increase the bleeding amount of the active compound during a given period of time, and molded articles shaped of the same polymer composition.

BEST MODE FOR CARRYING OUT THE INVENTION

The present invention provides a polymer composition comprising 100 parts by weight of an olefin-based polymer, and 0.01 to 100 parts by weight of a branched fatty acid and 0.01 to 200 parts by weight of a releasable active compound per 100 parts by weight of the olefin-based polymer.

The term "releasable" of "the releasable active compound" of the present invention means that the active compound bleeds from an molded article shaped of the polymer composition and oozes to the surface of the molded article.

The releasable active compound is an organic compound which exhibits its action relative to an insect-controlling, antibacterial, mildew-proofing, stain-proofing, weed-killing, plant growth-controlling, percutaneous treatment, rust-proofing, lubricating, surface-activating or antistatic effect. Such organic compounds may be used alone or in combination. As the releasable active compound, it is preferable to use a compound selected from the group consisting of insect-controlling agents, lubricants, antistatic agents and anti-fogging agents.

The amount of the releasable active compound to be added is preferably 0.01 part by weight or more, more preferably 0.1 part by weight or more, per 100 parts by weight of the olefin-based polymer contained in the polymer composition, from the viewpoint of the effect of the releasable active compound. Again, this amount is preferably 200 parts by weight or less, more preferably 100 parts by weight or less, still more preferably 50 parts by weight or less, per 100 parts by weight of the olefin-based polymer, from the viewpoint of suppressing stickiness of the resultant molded article.

When an insect-controlling agent is used as an organic compound having an insect-controlling activity, it is possible to use an insect-controlling compound such as an insecticide, an insect growth-controlling agent, an insect-repelling agent or the like. A compound which acts to enhance the effect of the insect-controlling agent i.e., a synergist) may be used in combination. Examples of the synergist include piperonyl butoxide, octachrolodipropylether, thiocyanoacetic isobornyl, N-(2-ethylhexyl)-bicyclo[2,2,1]-hepta-5-ene-2,3-dicarboxyimide, N-(2-ethylhexyl)-1-isopropyl-4-methylbicyclo[2,2,2]octo-5-ene-2,3-dicarboxyimide, etc.

Examples of the insecticide include pyrethroid-based compounds, organophosphorus-based compounds, carbamate-based compounds, phenyl pyrazole-based compounds, etc.

Examples of the pyrethroid-based compounds include permethrin, allethrin, d-allethrin, dd-allethrin, d-tetramethrin, prallethrin, cyphenothrin, d-phenothrin, resmethrin d-resmethrin, empenthrin, fenvalerate, esfenvalerate, fenpropathrin, cyhalothrin, cyfluthrin, etofenprox, tralomethrin, esbiothrin, benfluthrin, terallethrin, deltamethrin, phenothrin, tefluthrin, bifenthrin, cyfluthrin, cyphenothrin, cypermethrin, α-cypermethrin, etc. Examples of the organophosphorus-based compounds include fenitrothion, dichlorovos, naled, fenthion, cyanophos, chlorpyrifos, calcrofos, salithion, diazinon, etc. Examples of the carbamate-based compounds include methoxydiazon, propoxur, fenobucarb, carbaryl, etc. Examples of the phenyl pyrazole-based compound include fipronil, etc.

Examples of the insect growth-controlling agent include pyriproxfen, methoprene, hydroprene, diflubenzuron, cyromazine, phenoxycarb, lufenuron, etc.

Examples of the insect-repelling agent include diethyl toluamide, dibutyl phthalate, etc.

As the insect-controlling agent, an insecticide is preferable, and a pyrethroid-based compound is more preferable. In particular, a pyrethroid-based compound which shows a vapor pressure lower than $1 \times 10^{-6}$ mmHg at 25° C. is still more preferable. As such a pyrethroid-based compound, there are exemplified resmethrin, permethrin, etc.

Examples of insects to be controlled by the above-described insect-controlling agents are Arthropoda such as spiders, ticks and insects. The following are examples thereof: *Ormithonyssus sylviarum*, citrus red mite, *Tyrophagus putrescentiae*, etc. belonging to Acarina; and Atypus karshi, Pholcus phalangioides, etc. belonging to Araneae, in Arachnida: Thereuopoda clunifera, etc. belonging to Scutigeromorpha; and Bothropolys asperatus, etc. belonging to Lithobiomorpha in Chilopoda: and Oxidus gracilis, Nedyopus tambanus, etc. belonging to Polydesmoidea, in Chilopoda.

As the insects, the following are exemplified: Ctenolepisma villosa Escherich, etc. belonging to Thysanura; cave cricket, mole cricket, Teleogryllus emma, locusta migratoria, Schistocerca gregaria, locust, etc. belonging to Orthoptera; earwig, etc. belonging to Dermaptera; *Blattella germanica, Periplaneta fuliginosa, Periplaneta Japonica, Periplaneta americana*, etc. belonging to Blattaria; Japanese subterranean termite, Formosan subterranean termite, Incisitermes minor HAGEN, etc. belonging to Isoptera; Liposcelis entomophilus Enderlein, Liposcelis bostrychophilus Badonnel, etc. belonging to Psocoptera; Trichodectes canis, Felicola subrostratus, etc. belonging to Mallophaga; Pediculus humanus corporis, Pthirus pubis, Pediculus humanus, etc. belonging to Anoplura; Nilaparvata lugens Stal, Nephotettix cincticeps, Greenhous white fly, Myzus persicae, *Cimex lectularius Linnaeus*, Halyomorpha halys, etc. belonging to Hemiptera; dermestid beetles, Aulacophora femoralis, *Sitophilus zeamais, Lyctus brunmeus*, Ptinus japonicus, *Popillia japonica* Newman, etc. belonging to Coleoptera; cat flea, dog flea, human flea, etc. belonging to Siphonaptera; *Culex pipiens* pallens couguillett, Aedes aegypti, *anopheles*, Simuliidae, Chironomus, Psychodidae, House fly, Glossina palpalis, Tabanus trigonus, Syrphinae, etc. belonging to Diptera; Vespa, *Polistes*, Nesodiprion japonicus Marlatt, Dryocosmus kuriphilus, Sclerodermus nipponicus, Monomorium pharaonis, etc. belonging to Hymenoptera; and the like.

As the releasable active compounds which exhibit antibacterial, mildew-proofing, stain-proofing, weed-killing, plant growth-controlling, percutaneous treatment, rust-proofing, lubricating, anti-blocking, surface-activating and antistatic actions, there are exemplified commercially available antibacterial agents, mildew-proofing agents, stain-proofing agents, weed-killing agents, plant growth-controlling agents, percutaneous treating agents, rust-proofing agents, lubricants, surfactants, antistatic agents, etc.

As the lubricant, there are exemplified linear $C_{8-22}$ fatty acids, $C_{8-22}$ aliphatic alcohols, polyglycol, $C_{8-22}$ aliphatic amide, silicone oil, rosin derivatives, etc.

As the antistatic agent, there are exemplified $C_{8-22}$ fatty acid glycerin ester, sorbitan fatty acid ester, polyethylene glycol ester, etc.

As the anti-fogging agent, there are two types of anti-fogging agents: one is a solid at a room temperature (23° C.) and the other is a liquid at the same temperature. As the solid anti-fogging agent, there are exemplified nonionic surfactants. Examples of the nonionic surfactants include sorbitan fatty acid ester-based surfactants such as sorbitan monostearate, sorbitan monopalmitate, sorbitan monobehenate and sorbitan monomontanate; glycerin fatty acid ester-based surfactants such as glycerin monolaurate, glycerin monopalmitate and glycerin monostearate; polyethylene glycol-based surfactants such as polyethylene glycol monopalmitate and polyethylene glycol monostearate; alkylene oxide adducts of alkylphenol; esters of sorbitan/glycerin condensates and organic acids: and amine-based surfactants such as polyoxyethylene alkylamine compounds which include polyoxyethylene (2 mol) stearyl amine, polyoxyethylene (2 mol) lauryl amine, polyoxyethylene (4 mol) stearyl amine, etc.; fatty acid esters of polyoxyethylene alkylamine compounds, which include polyoxyethylene (2 mol) stearylamine monostearate, polyoxyethylene (2 mol) stearylamine distearate, polyoxyethylene (4 mol) stearyamine monostearate, polyoxyethylene (4 mol) stearyamine distearate, polyoxyethylene (8 mol) stearyamine monostearate, polyoxyethylene (2 mol) stearyamine monobehenate, polyoxyethylene (2 mol) laurylamine stearate, etc.; and fatty acid amines of polyoxyethylene alkylamine compounds, which include polyoxyethylene (2 mol) amide stearate, etc.

Examples of the anti-fogging agent which is a liquid at room temperature include glycerin-based fatty acid esters such as glycerin monooleate, diglycerin monooleate, diglycerin sesquioleate, tetraglycerin monooleate, hexaglycerin monooleate, tetraglycerin trioleate, hexaglycerin pentaoleate, tetraglycerin monolaurate and hexaglycerin monolaurate; and sorbitan fatty acid esters such as sorbitan monooleate, sorbitan dioleate and sorbitan monolaurate.

Examples of the antibacterial agent include alcohols such as ethanol; known antimicrobial active components such as hypochlorite, N-chloramines, iodine, peroxides, phenol compounds, hydroxybenzoic acid, bis(hydroxyphenyl)alkane, 8-hydroxyquinoline and derivatives thereof, quaternary ammonium-related compounds, pine oil compounds, carbamic acid and urea derivatives, ethylene oxide and propylene oxide; and known antibacterial agents such as phenols, halogen compounds, quaternary ammonium compounds, amine, alkanolamine, nitro derivatives, anilide, organosulfur, sulfur-nitrogen compounds, nalidixic acid and other quinolone carboxylic acid, nitrofuran and sulfonamide.

Examples of the antifungal agent include isothiazolone-based compounds and clathrate compounds of such isothiazolone-based compounds, in addition to the above-described known antimicrobial active components.

As the stain-proofing agent, known stain-proofing agents are exemplified. As the organotin compound, there are exemplified bis(tributyltin) oxide, tributyltin chloride, tributyltin fluoride, tributyltin acetate, tributyltin nicotinate, tributyltin versatate, bis(tributyltin)α,α'-dibromsuccinate, triphenyltin hydroxide, triphenyltin nicotinate, triphenyltin versatate, bis (triphenyltin)α,α'-dibromsuccinate, bis(triphenyltin) oxide, triphenyltin acetate, triphenyltin dimethyldithiocarbamate, etc.

As the weed-killing agents, there are exemplified triazine-based compounds such as atrazin and metribuzin; urea-based compounds such as fluometuron and isoproturon; hydroxybenzonitrile-based compounds such as bromoxynil and ioxynil; 2,6-dinitroaniline-based compounds such as pendimethalin and trifluraline; aryloxy-alkanoic acid-based compounds such as 2,4-D, dicamba, fluoroxypyr and mecoprop; sulfonylurea-based compounds such as bensulfuron-methyl, metsulfuron-methyl, nicosulfuron, primisulfulon-methyl and cyclosulfamuron; imidazolinone-based compounds such as imazapyl, imazaquin and imazethapyr; bispyribac sodium; bisthiobac sodium; acifluorfen sodium; surfentrazone; paraquat; flumetsulam, triflusulfuron-methyl, fenoxaprop-p-ethyl; cyhalofop butyl; diflufenican; norflurazon; isoxaflutole; glufocinate ammonium; glyphosate; bentazone; benthiocarb; mefenaset; propanil; flutiamide; etc.

As the plant growth-controlling agent, there are exemplified maleic hydrazide, chlormequat, ethephon, gibberellin, mepiquat chloride, thidiazuron, inabenfide, paclobutrazol, uniconazol, etc.

As the percutaneous treating agent, there are exemplified known pheromone-containing agents, pain-relief drugs, nicotine, etc.

As the corrosion-controlling agent, there are exemplified benzotriazole, dicyclohexylamine nitrite, tolyltriazole, etc.

The releasable active compound may be used as a releasable active compound support which is obtained by treating a support with the releasable active compound by way of retaining, carrying, impregnation, infiltration, injection, adsorption or absorption of the releasable active compound. As the support, there is used such one that allows retaining, carrying, absorption, adsorption, impregnation, infiltration or injection of the releasable active compound. Examples such a support include silica-based compounds, zeolites, clay minerals, metal oxides, mica, hydrotalcites, organic supports, etc. As the silica-based compounds, there are exemplified amorphous silica and crystalline silica. Examples thereof include powdered hydrated silica, fine hydrated silica, acid clay, diatom earth, quartz, white carbon, etc. As the zeolite, there are given A type zeolite, mordenite, etc. As the clay minerals, there are given montmorilonite, saponite, beidelite, bentonite, kaolinite, halloysite, nakhlite, dickite, anauxite, illite, sericite, etc. As the metal oxides, there are given zinc oxide, magnesium oxide, aluminum oxide, iron oxide, copper oxide, titanium oxide, etc. As the mica, there are given mica, vermiculite, etc. As the hydrotalcites, there are given hydrotalcite, smectite, etc. As the organic support, there are given charcoals (charcoal, turf, peat, etc.), polymer beads (microcrystalline cellulose, polystyrene beads, acrylic ester beads, methacrylic ester beads, polyvinylalcohol beads, etc.) and their crosslinked polymer beads. Besides, there are exemplified perlite, gypsum, ceramics, volcanic rock, etc.

As the olefin-based polymer to be used in the present invention, there are exemplified ethylene-based polymers, propylene-based polymers, butene-based polymers and 4-methyl-1-pentene-based polymers, and modified products, saponified products and hydrogenated products of these polymers. As the olefin-based polymer, two or more polymers selected from the above-described polymers may be used in combination.

As the ethylene-based polymer, there are exemplified polymers each of which comprises an ethylene-based monomer unit as a main unit (which usually contains 50% by mol or more of the ethylene-based monomer unit, based on 100% by mol of all the monomer units constituting the polymer), such as an ethylene homopolymer, an-ethylene-α-olefin copolymer, an ethylene-vinyl acetate copolymer, an ethylene-acrylic acid copolymer, an ethylene-acrylic ester copolymer, an ethylene-methacrylic acid copolymer, an ethylene-methacrylic ester copolymer, an ethylene-cyclic olefin copolymer, etc. As the ethylene homopolymer, there is given a low-density polyethylene, a medium-density polyethylene or a high-density polyethylene. As the α-olefin of the ethylene-α-olefin copolymer, there are exemplified $C_3$-$C_{20}$ α-olefins such as propylene, 1-butene, 1-pentene, 1-hexene, 1-heptene, 1-octene, 1-nonene, 1-decene, 1-dodecene, 4-methyl-1-pentene, 4-methyl-1-hexene, etc. As the ethylene-α-olefin copolymer, there are exemplified an ethylene-propylene copolymer, an ethylene-1-butene copolymer, an ethylene-1-hexene copolymer, an ethylene-1-octene copolymer, an ethylene-1-butene-1-hexene copolymer, etc.

As the propylene-based polymer, there are exemplified polymers each of which comprises a propylene-based monomer unit as a main unit (which usually contains 50% by mol or more of the propylene-based monomer unit, based on 100% by mol of all the monomer units constituting the polymer), such as a propylene homopolymer, a propylene-ethylene copolymer, a propylene-1-butene copolymer, a propylene-ethylene-1-butene copolymer, a propylene-cyclic olefin copolymer, etc. As the α-olefin of the propylene-α-olefin copolymer, there are exemplified $C_4$-$C_{20}$ α-olefins such as 1-butene, 1-pentene, 1-hexene, 1-heptene, 1-octene, 1-nonene, 1-decene, 1-dodecene, 4-methyl-1-pentene, 4-methyl-1-hexene, etc.

The olefin-based polymer is preferably an ethylene-based polymer, more preferably an ethylene-α-olefin copolymer.

The melt flow rate (MFR) of the olefin-based polymer is preferably 0.1 g/10 min. or more, more preferably 0.3 g/10 min. or more, still more preferably 0.5 g/10 min. or more, from the viewpoint of improvement on the external appearance of the resultant molded article. Again, the melt flow rate (MFR) of the olefin-based polymer is preferably 20 g/10 min. or less, more preferably 10 g/10 min. or less, still more preferably 5 g/10 min. or less, from the viewpoint of improvement on the mechanical strength of the resultant molded article. In this regard, the MFR of the propylene-based polymer is measured at 230° C. under a load of 21.18 N; and the MFRs of polymers other than the propylene-based polymer, i.e., the ethylene-based polymer and the butene-based polymer, are measured at 190° C. under a load of 21.18 N, according to the method regulated in JIS K7210-1995.

The density of the ethylene-based polymer is preferably 980 kg/m$^3$ or less, more preferably 970 kg/m$^3$ or less, still more preferably 960 kg/m$^3$ or less, from the viewpoint of facility to bleed the releasable active compound. Again, the density of the ethylene-based polymer is preferably 870 kg/m$^3$ or more, more preferably 875 kg/m$^3$ or more, still more preferably 880 kg/m$^3$ or more, from the viewpoint of improvement on the rigidity of the resultant molded article. In this regard, this density is measured as follows: that is, a test piece to be measured is annealed according to the method regulated in JIS K6760-1995, and is then measured with respect to its density according to the procedure regulated in the method A among the methods described in JIS K7112-1980.

The olefin-based polymer is produced in the presence of a known catalyst for polymerization of olefin, such as a Ziegler-Natta catalyst, a chromium-based catalyst, a metallocene-based catalyst, a radical polymerization catalyst, an organometal compound or the like, by a known polymerization method such as solution polymerization, slurry polymerization, vapor phase polymerization, high-pressure polymerization or the like. The polymerization method may be of batch type or continuous type, or may be two- or multi-step polymerization.

The branched fatty acid to be used in the present invention is a substance which has at least one carboxyl group and at least one carbon atom to be bonded to 3 or more carbon atoms. The branched fatty acid is preferably a $C_{4-30}$ branched fatty acid, more preferably a $C_{8-28}$ branched fatty acid. The number of branching of the fatty acid is not limited. Examples of the branched fatty acid include isobutyric acid, isovaleric acid, isocaproic acid, isocaprylic acid, isocapric acid, isolauric acid, isomyristic acid, isopalmitic acid, isostearic acid, isoarachidic acid, isobehenic acid, isolignoceric acid, etc. The bleeding amount of the releasable active compound is increased by addition of the branched fatty acid. The amount of the branched fatty acid to be added can be adjusted in accordance with a desired bleeding amount of the releasable active compound and a desired period of time for bleeding. The amount of the branched fatty acid to be added is preferably 0.01 part by weight or more, more preferably 0.1 part by weight or more, per 100 parts by weight of the olefin-based polymer, from the viewpoint of the effect to increase the bleeding amount. Again, this amount is preferably 100 parts by weight or less, more preferably 50 parts by weight or less, still more preferably 30 parts by weight or less, per 100 parts by weight of the olefin-based polymer, from the viewpoint of suppression of stickiness of the resultant molded article.

In the present invention, the branched fatty acid is a different compound from the releasable active compound.

The polymer composition of the present invention optionally may contain additives other than the branched fatty acid and the releasable active compound.

The polymer composition of the present invention can be obtained by melting and kneading the olefin-based polymer, the branched fatty acid and the releasable active compound by a known method. For example, a mixture of the olefin-based polymer, the branched fatty acid and the releasable active compound, prepared in advance, is molten and kneaded, using an extruder, a roll molding machine, a kneader or the like; the olefin-based polymer, the branched fatty acid and the releasable active compound are separately fed to an extruder, a roll molding machine, a kneader or the like, and are then molten and mixed; a mixture of the branched fatty acid and the releasable active compound, prepared in advance, and the olefin-based polymer are fed to an extruder, a roll molding machine, a kneader or the like, and are then molten and mixed; or a mixture of the olefin-based polymer and the branched fatty acid, prepared in advance, and the releasable active compound are separately fed to an extruder, a roll molding machine, a kneader or the like, and are then molten and kneaded. In case of melt-kneading by the use of an extruder, the molten mixture may be injected from the midway of the extruder, using an adding device such as a side extruder or a feeder.

The releasable active compound and the branched fatty acid may be used as a master batch admixed with a polymer, and this master batch may be molten and kneaded with the olefin-based polymer to thereby provide the polymer composition of the present invention. It is especially preferable to use the releasable active compound as a master batch admixed with a polymer.

As the polymer as the base of the master batch, there are exemplified olefin-based polymers such as an ethylene-based polymer, a propylene-based polymer, a butene-based polymer and a 4-methyl-1-pentene-based polymer, and modified products, saponified products and hydrogenated products of these polymers. Preferable examples thereof include a high-density polyethylene, a linear low-density polyethylene, a linear very-low-density polyethylene, a linear ultra-low-density polyethylene, a high-pressure processed low-density polyethylene, an ethylene-based polymer such as an ethylene-vinyl acetate copolymer or the like, a hydrogenated butadiene-based polymer, etc.

When the master batch is used to prepare the polymer composition, the amount of the master batch to be added is usually less than 50 parts by weight per 100 parts by weight of the olefin-based polymer contained in the polymer composition of the present invention. This amount is preferably 20 parts by weight or less, more preferably 10 parts by weight or less, from the viewpoint of improvement on cost-performance.

As the molding method for the polymer composition, there are exemplified known molding methods such as injection molding, extrusion molding, press molding, and slush molding (for powder). Otherwise, any of conventionally known processes employed for olefin-based polymers, such as multilayer extrusion molding, multicolor injection molding, composite spinning or extrusion laminate molding, may be appropriately selected for use in accordance with an end use, in other words, to improve the dynamic physical properties of the polymer composition in use, to increase the concentration of the releasable active compound in the surface of the resultant molded article, or to improve the moldability of the polymer composition. The layer formed of the polymer composition of the present invention in the resultant molded article may be arranged at any position in accordance with an end use.

Examples of the molded articles obtained by molding the polymer composition of the present invention include films, sheets, wall paper, curtains, floor materials, packing materials, hoses, tapes, tubes, pipes, bags, tents, turf, shop-curtains, blinds, electric wires, cables, sheaths, filaments, fibers, nets (mosquito nets, window screens, insect-proofing nets, etc.), yarns, ropes, filters, carpets, shoes, bags, clothes, electronic equipment, electric equipment, household appliances, business machine, vehicles, transport equipment, physical distribution materials such as containers and casings, materials for houses, parts of houses, and utensils for pets such as kennels, mats, sheets, collars and tags.

The effect of the present invention is especially remarkable in drawn molded articles among the above-described molded articles. The term "drawing" herein referred to means uniaxial or biaxial drawing of a molded article in a solid, semi-molten or molten state by a known method. For example, in shaping of filaments, a molded article extruded from an extruder is pulled and cooled to form thick filaments, which are then allowed to pass through a hot water bath and then are pulled at a higher speed than the speed of the former pulling, to thereby draw the filaments.

For example, in case of uniaxial drawing, a molded article from an extruder is pulled with a roll rotating at a speed of 1 m/sec., and the molded article is finally sampled with a roll rotating at a speed of 10 m/sec. In this case, the draw ratio is 10. In case of biaxial drawing, the draw ratio is a ratio of each of the sectional areas of a molded article found before and after drawing. In the above-described process for production of filaments, the molded article is allowed to pass through the hot water bath or the like between each of the rolls of which the pulling speeds are different from each other, so that heat is applied to the molded article so as to draw the molded article at a higher draw ratio. A higher draw ratio makes it possible to sustain the effect for increasing the bleeding amount of the releasable active compound by addition of the branched fatty acid. The draw ratio of the molded article is preferably 2 or more, more preferably 4 or more, still more preferably 6 or more. Too high a draw ratio induces a smaller breaking extension and a higher Young's modulus. Therefore, the draw ratio is preferably or less, more preferably 30 or less, still more preferably 20 or less, most preferably 15 or less, from the viewpoint of flexibility and elongation of the resultant filaments. The above-described drawing step is not necessarily carried out on the same line as the extrusion. That is, the drawing step alone may be independently carried out, and this drawing step may be done before a subsequent step, if any.

The polymer composition of the present invention is superior in melt-spinning property and sufficient in melt-extrudability, and thus is preferably used to produce filaments such as multifilaments and monofilaments. The polymer composition of the present invention is more preferably used to produce monofilaments. Filaments shaped of this polymer composition are superior in drawability under heating and sufficient in mechanical strength. Where filaments are produced using this polymer composition, it is possible to extrude and spin the polymer composition at a higher discharge rate and thus is possible to highly draw the resulting filaments in a one-step drawing operation. Therefore, the filaments can be produced at a lower cost.

As the method for shaping the polymer composition of the present invention into filaments, a known molding method such as the melt-spinning method, the (direct) spinning/drawing method or the like is employed. In concrete, an extruder or the like is used to melt the polymer composition and to extrude the molten polymer composition from a die nozzle via a gear pump to form a strand of the polymer composition; the melt-extruded strand-like polymer composition is pulled and is then cooled with a cooling medium such as water or an air for spinning; and then, optionally, the resulting filaments are drawn under heating, treated by heating and coated with an oil, and are then wound up.

The sectional shape of the filament is, for example, circular, elliptic, triangular, rectangular, hexagonal or star-shaped.

EXAMPLES

Hereinafter, the present invention will be described by way of Examples and Comparative Examples. In Examples and Comparative Examples, the physical properties were measured according to the following methods.

(1) Melt Flow Rate (MFR, g/10 Mins. in Unit)

A melt flow rate was measured at 190° C. under a load of 21.18 N according to the method regulated in JIS K7210-1995.

(2) Density ($kg/m^3$ in Unit)

A density was measured according to the procedure regulated in the method A among the methods described in JIS K7112-1980. A test piece to be measured was annealed according to the method for low-density polyethylene, regulated in JIS K6760-1995.

Example 1

(1) Preparation of Releasable Active Compound Support

Permethrin (Eksmin® manufactured by Sumitomo Chemical Company, Limited) as an insect-controlling agent was used as the releasable active compound. 2,6-Di-t-butyl-4-methylphenol (hereinafter referred to as AO-1) (1.5 parts by weight) as an antioxidant was dissolved in permethrin (51 parts by weight). Next, the mixture of permethrin and AO-1 (52.5 parts by weight) was stirred and mixed with amorphous silica as a support (Porous Silica® manufactured by Suzuki- Oil Co., Ltd.) (47.5 parts by weight) (i.e., 93.1 parts by weight per 100 parts by weight of permethrin) to obtain a releasable active compound support.

(2) Preparation of Polymer Composition

As an olefin-based polymer, there was used a mixture of pellets of a high-density polyethylene (HI-ZEX® 440M manufactured by PRIME POLYMER; MFR=0.9 g/10 mins.; density=948 $kg/m^3$) (100 parts by weight) and pellets of a high-pressure-processed low-density polyethylene (Sumikathene® G803 manufactured by Sumitomo Chemical Company, Limited) (hereinafter referred to as LD) (9.8 parts by weight) (hereinafter, this mixture being referred to as an olefin-based polymer mixture).

A polymer composition for filaments was prepared by melting and kneading the olefin-based polymer mixture (100 parts by weight), with an antioxidant, i.e., n-octadecyl-3-(3, 5-di-t-butyl-4-hydroxyphenyl)propionate (Irganox® 1076 manufactured by Ciba Specialty Chemicals K.K.) (0.013 part by weight), the releasable active compound support (4.4 parts by weight) and 2-heptylundecanoic acid (hereinafter referred to as isostearic acid 1) (1.4 parts by weight) as a branched fatty acid, per 100 parts by weight of the olefin-based polymer mixture, at about 150° C., using a Banbury mixer.

(3) Production of Monofilament

An extruder of 20 mmφ with a die having 4 holes of 1 mmφ was used to extrude the polymer composition for filaments, through the die set at 200° C. and at a discharge rate of 0.6 kg/hr. The resulting strand of the polymer composition was pulled at a line speed of 14 m/min. and was allowed to pass through a hot water bath, and was then pulled at a rate of 112 m/min.: that is, the draw ratio was 8. Thus, monofilaments with a fineness of 200 denier were obtained.

(4) Measurement of Bleeding Amount

The resultant monofilaments were stored in a thermostatic chamber set at 23° C. and were then taken out after 3 days, 7 days, 14 days, 28 days and 56 days had passed, respectively; and each time, acetone was used to cleanse the surfaces of the monofilaments to remove the bled substance therefrom, and the acetone used for cleansing was distilled off by blowing a nitrogen gas; and then, ethanol containing 50 ppm of triphenyl phosphate as an internal standard was used to again distribute permethrin, and a bleeding amount of permethrin was determined by gas chromatography.

The measurement by gas chromatography was conducted under the following conditions:

Injection amount: 1 μl
Column: a capillary column DB-1 (30 m in length,
  0.25 mm in inner diameter, and
  0.25 μm in thickness)
Detector: a hydrogen flame ionization detector (FID)
Temp. in vaporizing
chamber: 265° C.
Temp. of detector: 265° C.
Temp. of column: initially 50° C. for one min., and then, raised to 240° C. at a rate of 20° C./min.

A calibration curve for finding a ratio of a permethrin peak to an internal standard peak was made to determine a bleeding amount of permethrin.

The bleeding amount of permethrin was divided by the weight of the monofilament, and the resulting quotient was defined as the bleeding amount per the weight of the monofilament. The cleansed monofilament was again stored in the thermostat chamber set at 23° C. until the next measuring date. A cumulative bleeding amount of permethrin was calculated by adding the bleeding amounts found after 3 days (or 1 day), 7 days, 14 days, 28 days and 56 days had passed.

The cumulative bleeding amount of permethrin for 56 days was thus obtained. The result is shown in Table 1.

Comparative Example 1

A polymer composition was prepared in the same manner as in Example 1, except that zinc stearate was used instead of the isostearic acid 1. This polymer composition was used to produce monofilaments in the same manner as in Example 1, and the bleeding amounts of permethrin were measured. The result is shown in Table 1.

Comparative Example 2

A polymer composition was prepared in the same manner as in Example 1, except that myristic acid was used instead of the isostearic acid 1. This polymer composition was used to produce monofilaments in the same manner as in Example 1, and the bleeding amounts of permethrin were measured. The result is shown in Table 1.

Comparative Example 3

A polymer composition was prepared in the same manner as in Example 1, except that palmitic acid was used instead of the isostearic acid 1. This polymer composition was used to produce monofilaments in the same manner as in Example 1, and the bleeding amounts of permethrin were measured. The result is shown in Table 1.

Comparative Example 4

A polymer composition was prepared in the same manner as in Example 1, except that stearic acid was used instead of the isostearic acid 1. This polymer composition was used to produce monofilaments in the same manner as in Example 1, and the bleeding amounts of permethrin were measured. The result is shown in Table 1.

Comparative Example 5

A polymer composition was prepared in the same manner as in Example 1, except that behenic acid was used instead of the isostearic acid 1. This polymer composition was used to produce monofilaments in the same, manner as in Example 1. Measurement of the bleeding amounts of permethrin was made after 1 day, 7 days, 14 days, 28 days and 56 days had passed, respectively. The results were added, and the sum thereof was defined as the cumulative bleeding amount of permethrin for 56 days. The result is shown in Table 1.

Example 2

A polymer composition was prepared in the same manner as in Example 1, except that 2,2,4,8,10,10-hexamethylundecane-5-carboxylic acid (hereinafter referred to as isostearic acid 2) as a branched fatty acid was used instead of the isostearic acid 1. This polymer composition was used to produce monofilaments in the same manner as in Example 1, and the bleeding amounts of permethrin were measured. The result is shown in Table 1.

Example 3

A polymer composition was prepared in the same manner as in Example 1, except that 2-n-hexyldecanoic acid (hereinafter referred to as isopalmitic acid) as a branched fatty acid was used instead of the isostearic acid 1. This polymer composition was used to produce monofilaments in the same manner as in Example 1. Measurement of the bleeding amounts of permethrin was made after 1 day, 7 days, 14 days, 28 days and 56 days had passed, respectively. The results were added, and the sum thereof was defined as the cumulative bleeding amount of permethrin for 56 days. The result is shown in Table 1.

Example 4

Monofilaments were produced in the same manner as in Example 1, except that the pulling speed before the hot water bath was changed to a value indicated in Table 2, and that the monofilaments were not allowed to pass through the hot water bath; and the bleeding amounts of permethrin were measured. The monofilaments were not drawn, and thus, the draw ratio was assumed to be one (1) for convenience sake. Measurement of the bleeding amounts of permethrin was made after 1 day, 7 days, 14 days, 28 days and 56 days had passed, respectively. The results were added, and the sum thereof was defined as the cumulative bleeding amount of permethrin for 56 days. On the other hand, each of the bleeding amounts of permethrin which were measured after 1 day, 7 days, 14 days, 28 days and 56 days had passed, respectively, was divided by the weight of the monofilament and the number of days which had passed since the previous measuring date; and the resultant quotient was defined as a sequential bleeding amount of permethrin. As a reference day for this sequential bleeding amount, an interim day between the previous measuring date and the present measuring date was used. That is, the reference days for the bleeding amounts measured after 1 day, 7 days, 14 days, 28 days and 56 days had passed were 0.5 day, 4 days, 10.5 days, 21 days and 42 days after the previous measurement, respectively. Further, Comparative Example 6 in relation to a draw ratio, described later, was compared with the sequential bleeding amount found after 21 days had passed, and a ratio therebetween was calculated. The result is shown in Table 3.

Examples 5 to 7

Monofilaments were produced in the same manner as in Example 1, except that the pulling speeds before and after the hot water bath were changed to the values indicated in Table 2; and the bleeding amounts of permethrin were measured. A draw ratio was defined as a ratio of the pulling speeds found before and after the hot water bath. The bleeding amounts were measured after 1 day, 7 days, 14 day and 28 days had passed, respectively; each of the measured bleeding amounts was divided by the number of days which had been passed since the previous measuring date; the resulting bleeding amount per one day thus converted was defined as a sequential bleeding amount of permethrin. As a reference day for this sequential bleeding amount of permethrin, an interim day between the previous measuring date and the present measuring date was used. That is, sequential bleeding amounts of permethrin after 0.5 day, 4 days, 10.5 days and 21 days had passed were calculated based on the bleeding amounts of permethrin measured after 1 day, 7 days, 14 days and 28 days had passed. Further, each of Comparative Examples 7 to 9 in relation to the draw ratio, described later, was compared with the sequential bleeding amount measured after 21 days had passed, and their ratio was calculated. The results are shown in Table 3.

Comparative Example 6

A polymer composition was prepared in the same manner as in Example 1, except that zinc stearate was used instead of the isostearic acid 1. This polymer composition was used to produce monofilaments in the same manner as in Example 1. Measurement of the bleeding amounts of permethrin was made in the same manner as in Examples 4 to 7, to thereby calculate sequential bleeding amounts of permethrin. The result is shown in Table 3.

Comparative Examples 7 to 9

A polymer composition was prepared in the same manner as in Example 1, except that zinc stearate was used instead of the isostearic acid 1; and this polymer composition was used to produce monofilaments in the same manner as in Example 1, except that the pulling speeds before and after the hot water bath were changed to the values indicated in Table 2. Measurement of the bleeding amounts of permethrin was made in the same manner as in Examples 4 to 7, to thereby calculate sequential bleeding amounts of permethrin. The results are shown in Table 3.

TABLE 1

| | Fatty acid added | Cumulative bleeding amount of permethrin for 56 days (µg/g) |
|---|---|---|
| Ex. 1 | Isostearic acid 1 | 343 |
| C. Ex. 1 | Zinc stearate | 162 |
| C. Ex. 2 | Myristic acid | 141 |
| C. Ex. 3 | Palmitic acid | 154 |
| C. Ex. 4 | Stearic acid | 168 |
| C. Ex. 5 | Behenic acid | 176 |
| Ex. 2 | Isostearic acid 2 | 342 |
| Ex. 3 | Isopalmitic acid | 329 |

TABLE 2

| | Pulling speed (m/min.) before hot water bath | Pulling speed (m/min.) after hot water bath | Draw ratio | Denier |
|---|---|---|---|---|
| Ex. 4 | 13.9 | — | 1 | 655 |
| C. Ex. 6 | 14 | — | 1 | 764 |
| Ex. 5 | 14 | 56 | 4 | 204 |
| C. Ex. 7 | 14 | 56 | 4 | 200 |
| Ex. 6 | 14 | 112 | 8 | 200 |
| C. Ex. 8 | 14 | 112 | 8 | 204 |
| Ex. 7 | 12 | 120 | 10 | 203 |
| C. Ex. 9 | 12 | 120 | 10 | 200 |

TABLE 3

| | Sequential bleeding amount of permethrin (µg/g/day) | | | | Ratio of sequential bleeding amount after 21 days to Comparative Example |
|---|---|---|---|---|---|
| | 0.5 day | 4 days | 10.5 days | 21 days | |
| Ex. 4 | 2053 | 152 | 110 | 62 | 1.0 |
| C. Ex. 6 | 1081 | 130 | 116 | 62 | — |
| Ex. 5 | 443 | 138 | 84 | 42 | 1.2 |
| C. Ex. 7 | 343 | 126 | 66 | 36 | — |
| Ex. 6 | 135 | 14.3 | 9.3 | 4.0 | 1.8 |
| C. Ex. 8 | 57 | 7.9 | 4.4 | 2.3 | — |
| Ex. 7 | 113 | 9.2 | 5.6 | 2.8 | 2.2 |
| C. Ex. 9 | 44 | 4.0 | 2.1 | 1.3 | — |

The invention claimed is:

1. A polymer composition comprising 100 parts by weight of an olefin-based polymer, and 0.01 to 100 parts by weight of a branched fatty acid and 0.01 to 200 parts by weight of one or more releasable active compounds per 100 parts by weight of said olefin-based polymer, wherein the olefin-based polymer has a melt flow rate of 0.1 to 20 g/10 mins, wherein the polymer composition is prepared by melting and kneading the olefin-based polymer, the branched fatty acid, and the one or more releasable active compounds,
wherein said one or more releasable active compounds comprise a pyrethroid-based compound, and
wherein said branched fatty acid is isostearic acid or isopalmitic acid.

2. The polymer composition of claim 1, wherein said releasable active compounds further comprises a compound selected from the group consisting of additional insect-controlling agents, lubricants, antistatic agents and anti-fogging agents.

3. The polymer composition of claim 1, wherein said releasable active compound is a pyrethroid-based compound.

4. The polymer composition of claim 1, wherein said olefin-based polymer is an ethylene-based polymer.

5. The polymer composition of claim 4, wherein said ethylene-based polymer is an ethylene-α-olefin copolymer; and wherein the density of said copolymer is from 870 to 980 kg/m$^3$, and the melt-flow rate thereof, from 0.1 to 20 g/10 mins.

6. A molded article shaped of the polymer composition defined in claim 1.

7. The molded article of claim 6, drawn at a draw ratio of 2 or more.

8. The molded article of claim 7, which is a filament.

9. A mosquito net made of the filament defined in claim 8.

10. A solid article comprising the polymer composition of claim 1.

11. The polymer composition of claim 1, wherein a bleeding amount of the releasable active compound is at least 329 µg/g over 56 days.

* * * * *